United States Patent
Matsunaga et al.

(10) Patent No.: US 10,639,969 B2
(45) Date of Patent: May 5, 2020

(54) AIR CONDITIONER FOR VEHICLE

(71) Applicant: DENSO CORPORATION, Kariya, Aichi-pref. (JP)

(72) Inventors: Kouji Matsunaga, Kariya (JP); Takuya Nagao, Kariya (JP); Eiichi Ogata, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 58 days.

(21) Appl. No.: 15/776,579

(22) PCT Filed: May 23, 2016

(86) PCT No.: PCT/JP2016/065152
§ 371 (c)(1),
(2) Date: May 16, 2018

(87) PCT Pub. No.: WO2017/085954
PCT Pub. Date: May 26, 2017

(65) Prior Publication Data
US 2018/0370334 A1    Dec. 27, 2018

(30) Foreign Application Priority Data

Nov. 20, 2015  (JP) .................................. 2015-227983

(51) Int. Cl.
*B60H 3/00* (2006.01)
*A61L 9/22* (2006.01)
*B60H 1/00* (2006.01)

(52) U.S. Cl.
CPC .............. *B60H 3/0078* (2013.01); *A61L 9/22* (2013.01); *B60H 1/00007* (2013.01);
(Continued)

(58) Field of Classification Search
CPC ..... A61L 9/22; B60H 3/0078; B60H 1/00064; B60H 1/00514
See application file for complete search history.

(56) References Cited

U.S. PATENT DOCUMENTS

2008/0251236 A1    10/2008   Byon et al.
2013/0206382 A1*   8/2013   Ichishi ................. B60N 2/5628
                                                                 165/203

FOREIGN PATENT DOCUMENTS

JP        2006010220 A      1/2006
JP        2009248715 A     10/2009
(Continued)

*Primary Examiner* — Sean E Conley
(74) *Attorney, Agent, or Firm* — Harness, Dickey & Pierce, P.L.C.

(57) ABSTRACT

An air conditioner for a vehicle includes: an air-conditioning case having therein an air flow passage through which air toward the vehicle interior flows, and an outlet opening formed at an upper part of the air-conditioning case and through which the air toward the vehicle interior passes; a heat exchanger disposed on a lower side of the outlet opening inside the air-conditioning case to exchange heat between air toward the vehicle interior and a heat-exchange medium; and an ion generator that includes electrodes to generate ions. The ion generator is mounted on the air-conditioning case such that the electrodes are exposed in air flowing through the air flow passage. The air-conditioning case has a collision-side wall surface with which the airflow having passed through the heat exchanger collides to be directed upward, and a lateral-side wall surface connected to and laterally adjacent to the collision-side wall surface. The ion generator is disposed at a predetermined position of the collision-side wall surface or the lateral-side wall surface.

8 Claims, 8 Drawing Sheets

(52) U.S. Cl.
CPC ..... *B60H 1/00064* (2013.01); *B60H 1/00514* (2013.01); *A61L 2209/16* (2013.01); *B60H 2001/00135* (2013.01)

(56) References Cited

FOREIGN PATENT DOCUMENTS

| | | | |
|---|---|---|---|
| JP | 2009295359 | A | 12/2009 |
| JP | 2011105257 | A | 6/2011 |
| JP | 2011126541 | A | 6/2011 |
| JP | 2014202421 | A | 10/2014 |

\* cited by examiner

AIR CONDITIONER FOR VEHICLE

CROSS REFERENCE TO RELATED APPLICATIONS

This application is a U.S. National Phase Application under 35 U.S.C. 371 of International Application No. PCT/JP2016/065152 filed on May 23, 2016 and published in Japanese as WO 2017/085954 A1 on May 26, 2017. This application is based on and claims the benefit of priority from Japanese Patent Application No. 2015-227983 filed on Nov. 20, 2015. The entire disclosures of all of the above applications are incorporated herein by reference.

FIELD OF THE INVENTION

The present disclosure relates to an air conditioner for a vehicle that includes an ion generator.

BACKGROUND ART

Patent Document 1 discloses a vehicle air conditioner that includes an ion generator mounted on an air-conditioning case. In the vehicle air conditioner, the ion generator is disposed at a partition that separates a passage communicating with a defroster opening and a passage communicating with a face opening.

RELATED ART DOCUMENT

Patent Document

[Patent Document 1] Japanese Unexamined Patent Application Publication No. 2009-248715

SUMMARY OF THE INVENTION

There are some vehicle air conditioners in which the inside of the air-conditioning case is configured to bend an airflow passing through a heat exchanger toward the upper side.

In this type of vehicle air conditioner, a face opening and a defroster opening are formed at upper parts of the air conditioning case. On the lower side of the face opening and the defroster opening inside the air-conditioning case, a cooling heat exchanger and a heating heat exchanger are disposed. An air passage inside the air-conditioning case is configured to bend the airflow passing through the cooling heat exchanger and the airflow passing through the heating heat exchanger toward the upper side. Such a layout of the inside of the air-conditioning case enables the air-conditioning case to be mounted within the vehicle interior in a compact manner.

When the ion generator is mounted on such an air-conditioning case of the vehicle air conditioner, if the air hitting electrodes of the ion generator is weak, the ion generator cannot discharge many ions. Consequently, ions cannot be effectively delivered to the vehicle interior.

Therefore, it is an object of the present disclosure to provide an air conditioner for a vehicle which can effectively deliver ions into the vehicle interior.

According to an example of the disclosure, an air conditioner for a vehicle, for blowing air with ions into a vehicle interior, the air conditioner includes: an air-conditioning case that defines therein an air flow passage through which air toward the vehicle interior flows, and has an outlet opening at an upper part of the air-conditioning case and through which the air toward the vehicle interior passes; a heat exchanger disposed at a lower side of the outlet opening in the air-conditioning case, the heat exchanger being configured to exchange heat between air toward the vehicle interior and a heat-exchange medium; and an ion generator that includes electrodes configured to generate ions, the ion generator being mounted on the air-conditioning case such that the electrodes are exposed in the air flowing through the air flow passage. The air-conditioning case has a collision-side wall surface with which an airflow having passed through the heat exchanger collides to be directed upward, and a lateral-side wall surface connected to and laterally adjacent to the collision-side wall surface. Furthermore, the ion generator is disposed at a predetermined position of the collision-side wall surface or the lateral-side wall surface.

When the airflow having passed through the heat exchanger collides with the collision-side wall surface to change its direction upward, the airflow at a part where its direction is changed by colliding in the air flow passage on the downstream side of the heat exchanger has the highest flow speed in the vicinity of the collision-side wall surface. Even in another part of the air flow passage on the downstream side of the heat exchanger, which is located on the downstream side with respect to the part where the airflow collides to change its direction, the air flows upward while part of the airflow with a high flow speed is being attached to the collision-side wall surface by the Coanda effect. Thus, the flow speed of the airflow having passed through the heat exchanger becomes highest in the vicinity of the collision-side wall surface and the lateral-side wall surfaces. The reason why the flow speed of the airflow in vicinity of the lateral-side wall surfaces becomes high is that the airflow flowing through the vicinity of the collision-side wall surface at a high flow speed spreads over the vicinity of the lateral-side wall surfaces.

Therefore, according to the present disclosure, the ion generator is disposed at the part where the flow speed of the airflow is high, thereby making it possible to strength air hitting the electrodes of the ion generator. Consequently, many ions can be discharged from the ion generator. Thus, the ions can be effectively delivered to the vehicle interior.

DESCRIPTION OF EMBODIMENTS

Figure 1:
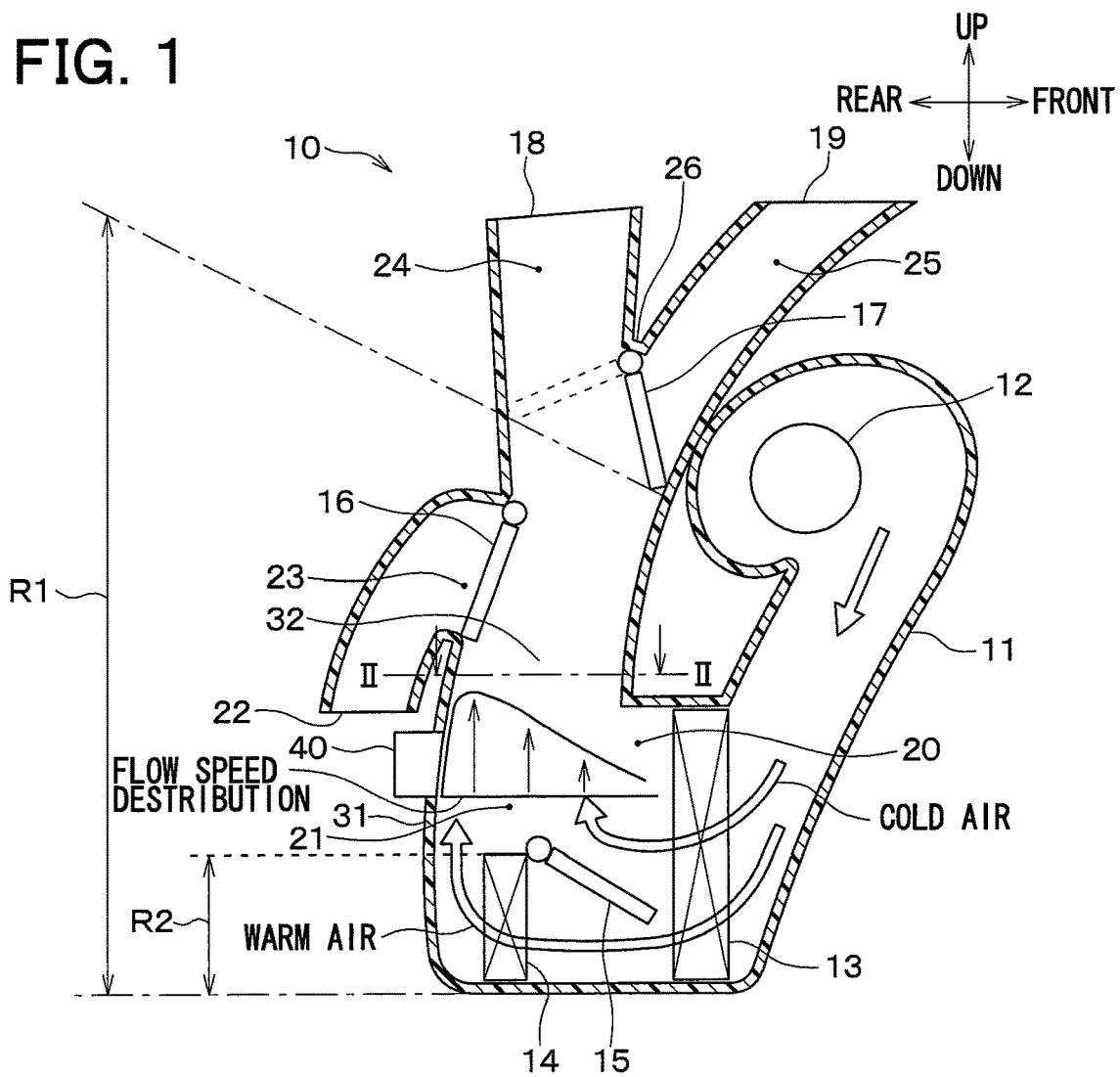
FIG. 1 is a cross-sectional view of an interior air-conditioning unit in a first embodiment.

In the following, embodiments of the present disclosure will be described with reference to the accompanying drawings. In the respective embodiments below, the same or equivalent parts will be described with the same reference characters. The arrows indicative of the front, rear, upward, and downward in figures represent the directions of the interior air-conditioning unit in the vehicle-mounted state with respect to the vehicle.

First Embodiment

A vehicle air conditioner in the present embodiment includes an interior air-conditioning unit 10 shown in FIG. 1. The interior air-conditioning unit 10 includes an air-conditioning case 11, a fan 12, an evaporator 13, a heater core 14, an air mix door 15, a foot door 16, and a face/defroster switching door 17.

The air-conditioning case 11 accommodates therein the fan 12, the evaporator 13, the heater core 14, the air mix door 15, the foot door 16, and the face/defroster switching door 17. The air-conditioning case 11 forms therein an air flow passage through which air flows toward the vehicle interior. In an upper part of the air-conditioning case 11, a face opening 18 and a defroster opening 19 are formed. The face opening 18 and the defroster opening 19 are outlet openings through which the air directed towards the vehicle interior passes. Further, an air introduction port (not shown) is formed in the upper part of the air-conditioning case 11.

The fan 12 configures a blower that draws air from an air introduction port and forms the airflow directed toward the vehicle interior inside the air-conditioning case 11. The fan 12 is disposed on the front side and the upper side in the air-conditioning case 11.

The evaporator 13 is a cooling heat exchanger that cools the air by exchanging heat between the air directed toward the vehicle interior and a refrigerant as a heat-exchange medium. The evaporator 13 configures a vapor compression refrigeration cycle together with a compressor, a heat radiator, and an expansion valve (all not shown). The evaporator 13 evaporates the refrigerant by the heat exchange with the air. The evaporator 13 is disposed on the lower side of the face opening 18, the defroster opening 19, and the fan 12 inside the air-conditioning case 11.

The heater core 14 is a heating heat exchanger that heats the air by exchanging heat between the air directed toward the vehicle interior and an engine coolant as a heat-exchange medium. The heater core 14 is disposed on the lower side of the face opening 18, the defroster opening 19, and the fan 12 inside the air-conditioning case 11. Further, the heater core 14 is disposed on the rear side with respect to the evaporator 13. The heater core 14 heats the air having passed through the evaporator 13.

The air mix door 15 is a member that adjusts the ratio of the airflow passing through the heater core 14 to the airflow flowing while bypassing the heater core 14. The air mix door 15 is disposed between the evaporator 13 and the heater core 14.

A cold-air flow passage 20 is formed on the upper side of the heater core 14 inside the air-conditioning case 11 to cause the air passing through the evaporator 13 to flow while bypassing the heater core 14. An air mix portion 21 is formed on the upper side of the heater core 14 and on the rear side of the cold-air flow passage 20 inside the air-conditioning case 11. The air mix portion 21 is a part where the airflow flowing through the heater core 14 and the airflow flowing while bypassing the heater core 14 are merged and mixed together.

A foot communication port 23 that communicates with a foot opening 22 is formed on the upper side of the air mix portion 21 and on the lower side of the face/defroster switching door 17 inside the air-conditioning case 11. The foot communication port 23 is formed at a rear wall surface 31 to be described later. The foot door 16 that opens and closes the foot communication port 23 is disposed on the upstream side of the foot communication port 23.

A face flow passage 24 and a defroster flow passage 25 are formed on the upper side inside the air-conditioning case 11. The face flow passage 24 guides the air toward the face opening 18. The defroster flow passage 25 guides the air toward the defroster opening 19. In other words, the air-conditioning case 11 includes a partition 26 that separates the face flow passage 24 and the defroster flow passage 25. The face/defroster switching door 17 is disposed on the upstream side of the partition 26. The face/defroster switching door 17 is a door that switches between opening and closing of each of the face opening 18 and the defroster opening 19.

The face opening 18 communicates with a face air outlet that is provided in the vehicle interior to blow out the air toward the upper body of an occupant. The defroster opening 19 communicates with a defroster air outlet that is provided in the vehicle interior to blow out the conditioned air toward the window glass of the vehicle. The foot opening 22 communicates with a foot air outlet (not shown) for blowing out the air toward the lower body of an occupant.

Figure 2:
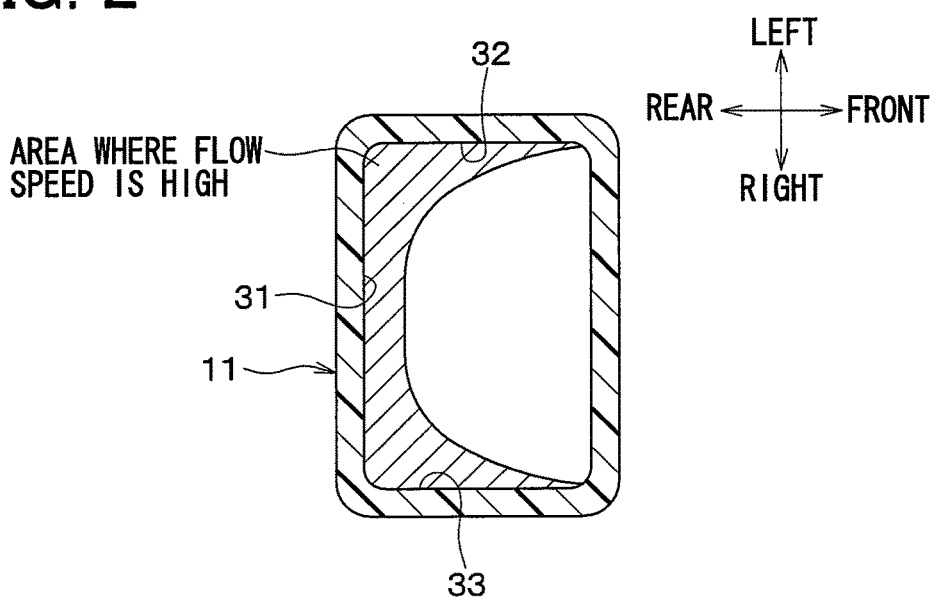
FIG. 2 is a cross-sectional view taken along the line II-II of FIG. 1.

As shown in FIG. 2, the air-conditioning case 11 has the rear wall surface 31 positioned on the vehicle rear side of the vehicle and lateral-side wall surfaces 32 and 33 positioned on both sides in the right-left direction of the vehicle, as wall surfaces configuring a downstream side flow passage on the downstream side of the airflow with respect to the evaporator 13 and the heater core 14. The rear wall surface 31 extends along the up-down direction and the right-left direction of the vehicle. The lateral-side wall surfaces 32 and 33 extend along the up-down direction and the front-rear direction of the vehicle. The rear wall surface 31 and the lateral-side wall surfaces 32 and 33 extend from the bottom part to the upper part of the air-conditioning case 11.

In the air-conditioning case 11 having such a layout, the air flows downward from the fan 12. When cold air and warm air are mixed together in a face mode, the air from the fan 12 passes through the evaporator 13 and the heater core 14 in the lateral direction from the front side to the rear side, and then changes its direction to the upward direction to flow toward the face opening 18. That is, the warm air passing through the heater core 14 in the lateral direction and the cold air passing through the evaporator 13 in the lateral direction while bypassing the heater core 14 change their respective directions to the upward direction to flow toward the face opening 18.

When the airflow passing through the heater core 14 and the airflow bypassing the heater core 14 are formed, the airflow passing through the heater core 14 and the airflow bypassing the heater core 14 collide with the rear wall surface 31 to change their directions upward. When air does not pass through the heater core 14 (that is, when the position of the air mix door 15 is located at the maximum air-cooling position), the airflow passing only through the evaporator 13 but not the heater core 14 collides with the rear wall surface 31 positioned on the vehicle rear side to change its direction upward. When all air having passed through the evaporator 13 passes through the heater core 14 (that is, when the position of the air mix door 15 is located at the maximum air-heating position), the airflow passing only through the heater core 14 collides with the rear wall surface 31 positioned on the vehicle rear side to change its direction upward. Therefore, in the present embodiment, the rear wall surface 31 configures a collision-side wall surface with which the airflow having passed through the heat exchanger collides to be directed upward.

In the interior air-conditioning unit 10 of the present embodiment, an ion generator 40 is mounted on the rear wall surface 31. A mounting position of the ion generator 40 is a predetermined position within a range R1 that is located on the upper side with respect to the lower end portion of the heater core 14 and on the upstream side of the airflow (i.e., on the lower side) with respect to the partition 26 and a movable region of the face/defroster switching door 17. Specifically, the mounting position of the ion generator 40 is located at the rear wall surface 31 on the downstream side of the airflow with respect to a range R2 of the rear wall surface 31 facing the heater core 14 via a space in the airflow direction inside the heater core 14 and on the upstream side of the airflow with respect to the foot communication port 23.

Figure 3:
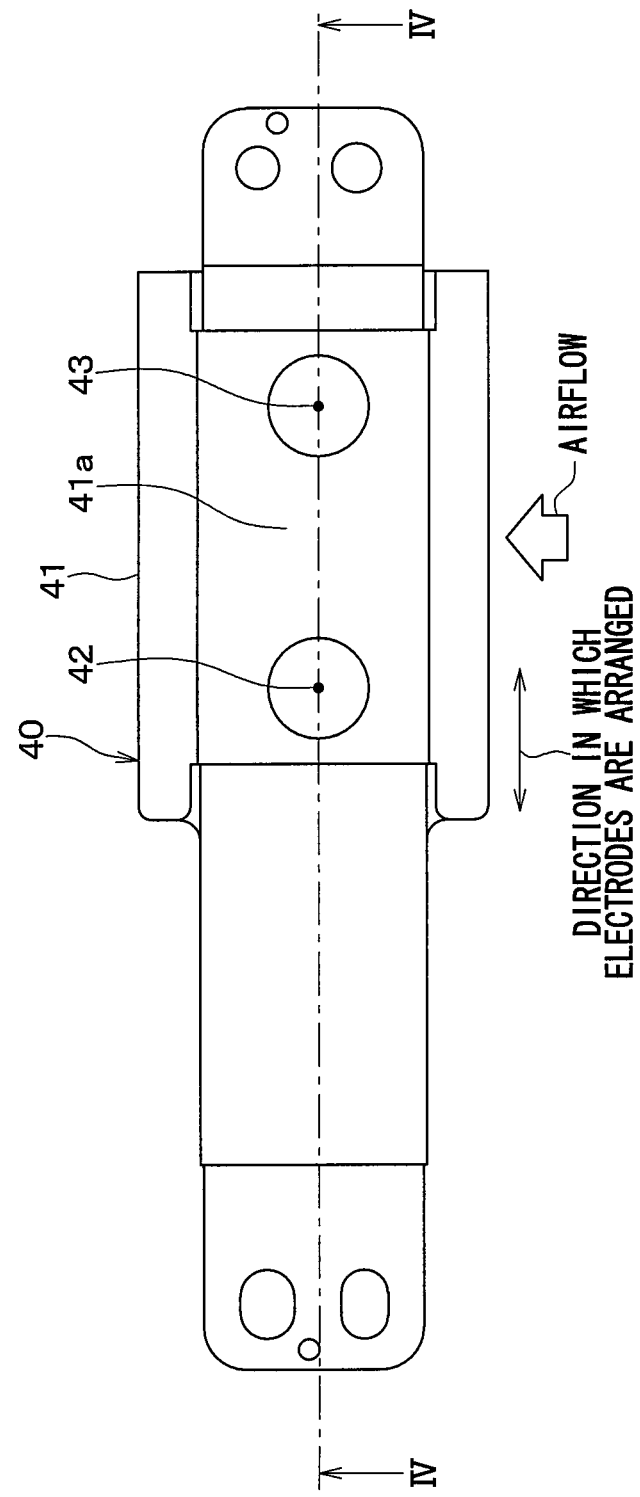
FIG. 3 is a plan view of an ion generator in the first embodiment.
Figure 4:
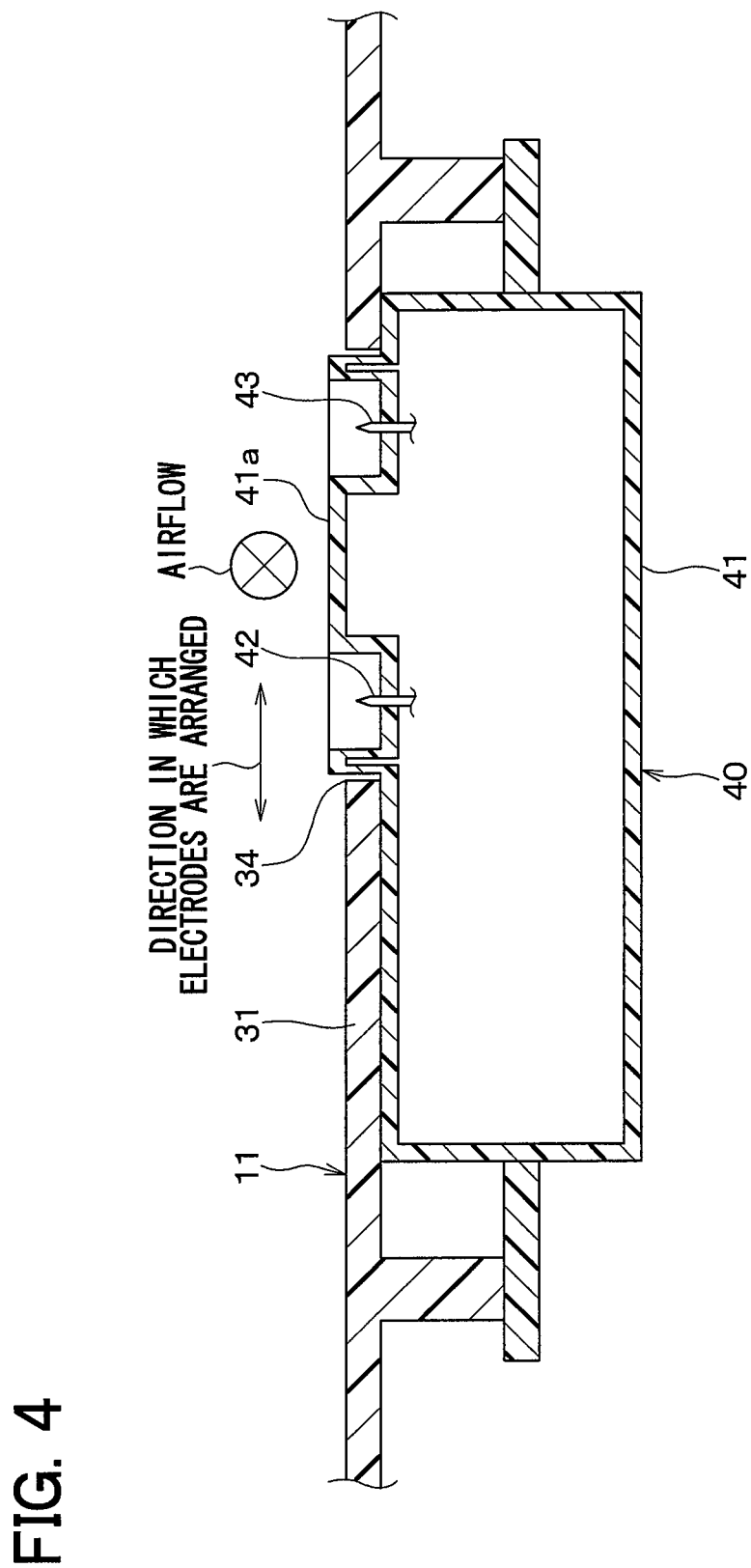
FIG. 4 is an enlarged view of the ion generator and its surroundings shown in FIG. 1, specifically, a cross-sectional view of the ion generator taken along the line IV-IV of FIG. 3.

As shown in FIGS. 3 and 4, the ion generator 40 includes a main body 41 and discharge electrodes 42 and 43 formed in an electrode formation portion 41*a* of the main body 41. The ion generator 40 has, as the discharge electrodes, one anode (i.e., positive electrode) 42 and one cathode (i.e., negative electrode) 43. The anode 42 and the cathode 43 are separated from each other. FIG. 4 omits the inside of the main body 41.

In the ion generator 40, a positive voltage is applied to the anode 42 to discharge an electrical current, while a negative voltage is applied to the cathode 43 to discharge an electrical current. Thus, plasma is formed from each of the anode 42 and the cathode 43. By such plasma, positive ions are formed around the anode 42, while negative ions are formed around the cathode 43. The ion generator 40 exhibits the effect of decomposing and removing mold fungi and viruses floating within a vehicle interior space in the air by using both the positive and negative ions.

As shown in FIG. 4, a mounting opening 34 is formed at the rear wall surface 31. The ion generator 40 is mounted on the rear wall surface 31 with the electrode formation portion 41*a* inserted into the mounting opening 34. The position of the surface of the electrode formation portion 41*a* is substantially at the same level as the position of the rear wall surface 31. Thus, the anode 42 and the cathode 43 are configured to be exposed in air flowing through the air flow passage.

As shown in FIGS. 3 and 4, the anode 42 and the cathode 43 are arranged in a direction that intersects the direction of the airflow (specifically, a main flow) toward the face opening 18 and the defroster opening 19. In FIG. 4, the direction perpendicular to the paper surface indicates a direction of the airflow. In the present embodiment, the anode 42 and the cathode 43 are arranged in the direction vertical to the direction of the airflow directed from the lower side to the upper side. That is, the anode 42 and the cathode 43 are arranged side by side in the right-left direction.

As mentioned above, the interior air-conditioning unit 10 of the present embodiment has a layout of the inside of the air-conditioning case 11 in which the airflow passing through the heater core 14 and the airflow bypassing the heater core 14 collide with the rear wall surface 31 to change their directions upward. In the interior air-conditioning unit 10 of the present embodiment, the ion generator 40 is mounted on the rear wall surface 31.

Inside the air-conditioning case 11 with the above-mentioned layout, the airflows having passed through the evaporator 13 and the heater core 14 are directed toward the rear wall surface 31. Thus, as illustrated by the flux distribution in FIG. 1, the flow speed of the airflow at a part of the downstream-side flow passage on the airflow downstream side of each of the evaporator 13 and the heater core 14 where the direction of the airflow is changed upward becomes highest in the vicinity of the rear wall surface 31. Even in a part of the downstream-side flow passage, which is located on the downstream side of the airflow with respect to the part where the airflow changes its direction upward, the air still flows upward while part of its airflow with a high flow speed is being attached to the rear wall surface 31 by the Coanda effect.

Thus, as shown in FIG. 2, the flow speed of the airflow having passed through the evaporator 13 and the heater core 14 becomes highest in the vicinity of the rear wall surface 31 and lateral-side wall surfaces 32 and 33. The reason why the flow speed of the airflow in vicinity of the lateral-side wall surfaces 32 and 33 becomes high is that the airflow flowing at a high flow speed through the vicinity of the rear wall surface 31 spreads over the vicinity of the lateral-side wall surfaces 32 and 33. A shaded area in FIG. 2 indicates an area where the flow speed of the airflow in the air-conditioning case 11 is high.

Therefore, according to the present embodiment, the ion generator 40 is disposed at the part where the flow speed of the airflow is high, thereby making it possible to strengthen air hitting the discharge electrodes 42 and 43 of the ion generator 40. In this way, ions can be discharged sufficiently from the ion generator 40. Thus, these ions can be effectively delivered to the vehicle interior.

In the present embodiment, the ion generator 40 is disposed on the downstream side of the airflow with respect to the evaporator 13 and the heater core 14. Thus, air with ions can be avoided from colliding with the inner wall (for example, fins) of a heat exchanger, such as the evaporator 13 and the heater core 14, thus preventing the ions from disappearing there.

In the present embodiment, the ion generator 40 is disposed on the upstream side of the airflow with respect to the partition 26 and a face/defroster switching door 17. Thus, even if the ion generator 40 is not disposed corresponding to each of the face opening 18 and the defroster opening 19, the air with ions can be blown out to the vicinity of the occupant's face in either the face mode of blowing the air from the face opening 18 into the vehicle interior or the defroster mode of blowing the air from the defroster opening 19 into the vehicle interior.

When the airflow having passed through the heater core 14 changes its direction upward, part of the airflow through the heater core 14 collides with the part of the rear wall surface 31 facing the heater core 14, while the other part of the airflow flows along the part of airflow changing its direction after the collision. For this reason, if the mounting position of the ion generator 40 is within the range R2 of the rear wall surface 31 facing the heater core 14, some of the ions generated by the ion generator 40 will collide with the rear wall surface 31 to disappear.

In contrast, in the present embodiment, the mounting position of the ion generator 40 is located on the downstream side of the airflow with respect to the range R2 of the rear wall surface 31 facing the heater core 14. That is, the mounting position of the ion generator 40 is located in a part of the rear wall surface 31 on the downstream side of the airflow with respect to a part of the rear wall surface 31 with which the airflow having passed through the heater core 14 collides. Thus, some of ions generated by the ion generator 40 can be prevented from colliding with the rear wall surface 31 and disappearing there. The mounting position of the ion generator 40 may be located on the upper side with respect to the heater core 14. This mounting position can provide the same effects.

In the present embodiment, the anode 42 and the cathode 43 of the ion generator 40 are arranged in a direction that intersects the direction of the airflow toward the face opening 18 and the defroster opening 19. Thus, positive ions discharged from the anode 42 can be prevented from flowing to the cathode 43 to disappear at the cathode 43. Likewise, negative ions discharged from the cathode 43 can be prevented from flowing to the anode 42 to disappear at the anode 42. Thus, a large amount of ions can be discharged from each of the anode 42 and the cathode 43.

In the interior air-conditioning unit 10 of the present embodiment, the fan 12 is disposed at the same position in the left-right direction with respect to the evaporator 13 and the heater core 14, but may be disposed while being offset in the left-right direction with respect to the evaporator 13 and the heater core 14.

Second Embodiment

An interior air-conditioning unit 10 of the present embodiment differs from that of the first embodiment in the mounting position of the ion generator 40, but is the same as that of the first embodiment in other structures.

Figure 5:
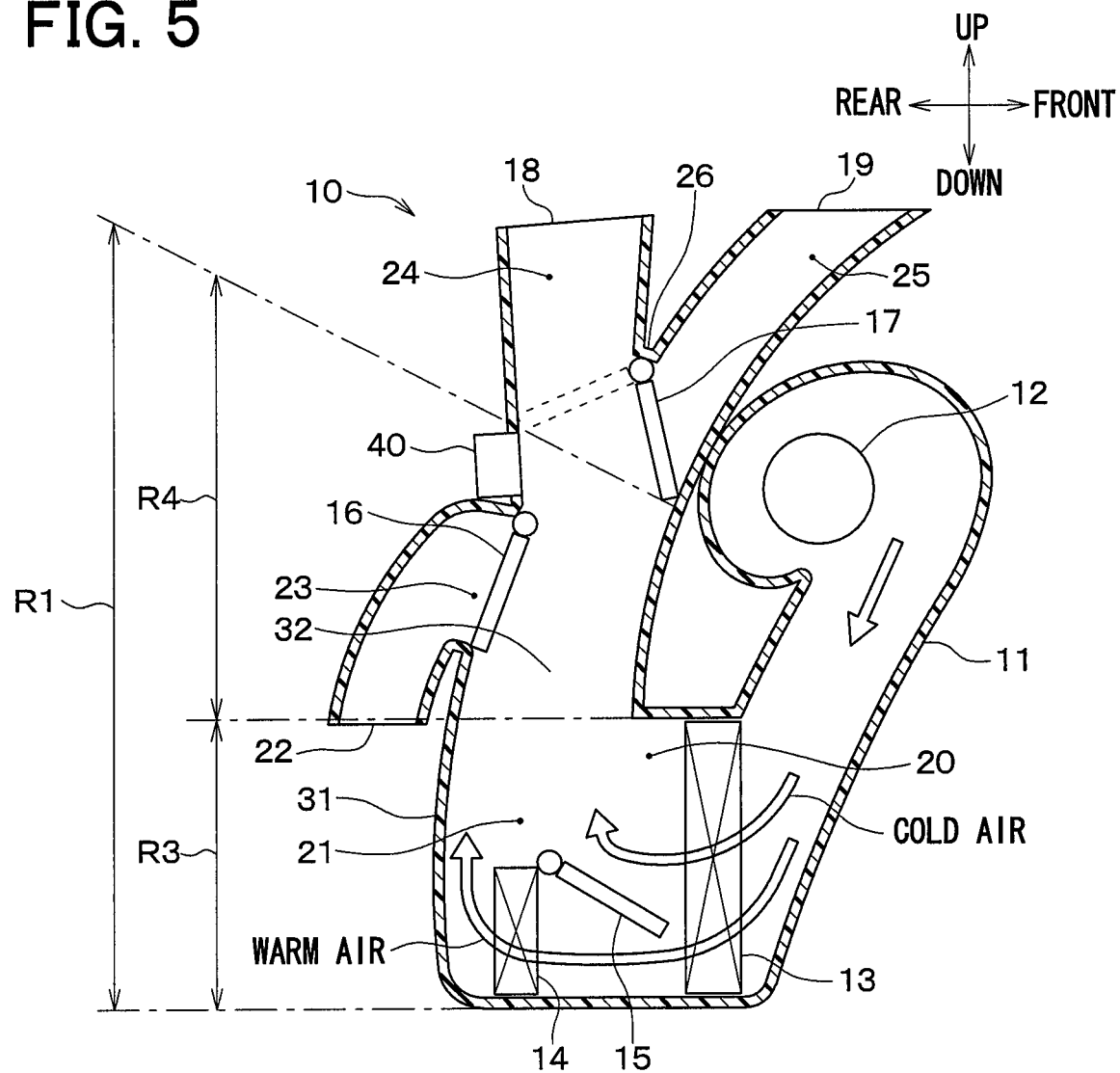
FIG. 5 is a cross-sectional view of an interior air-conditioning unit in a second embodiment.

As shown in FIG. 5, in the interior air-conditioning unit 10 of the present embodiment, the mounting position of the ion generator 40 is located in a part of the rear wall surface 31 directly close to the upstream side of the airflow with respect to the face/defroster switching door 17. In other words, the mounting position of the ion generator 40 is located in a part of the rear wall surface 31 on the downstream side of the airflow with respect to the foot communication port 23 and on the upstream side of the airflow with respect to the partition 26 and the face/defroster switching door 17. As mentioned in the first embodiment, the airflow having passed through the evaporator 13 and the heater core 14 flows upward while part of the airflow with a high flow speed is being attached to the rear wall surface 31, after changing its direction upward. Thus, the present embodiment can also obtain the same effects as the first embodiment.

In the present embodiment, the mounting position of the ion generator 40 is located on the upper side with respect to the evaporator 13 and the heater core 14. That is, the mounting position of the ion generator 40 is located in the position on the downstream side of the airflow with respect to the part of the rear wall surface 31 with which the airflow having passed through the evaporator 13 and the heater core 14 collides. In more detail, the mounting position of the ion generator 40 is located on the downstream side of the airflow with respect to a range R3 of the rear wall surface 31 and within a range R4 on the upstream side of the airflow with respect to the movable regions of the partition 26 and the face/defroster switching door 17. Here, the range R3 faces the heater core 14 via a space in the direction of the airflow in the heater core 14, and faces the evaporator 13 via a space in the direction of the airflow in the evaporator 13.

Thus, when the position of the air mix door 15 is located at a maximum cooling position, ions generated by the ion generator 40 can be avoided from disappearing due to collision of part of the cold air, flowing through the cold-air flow passage 20, with the rear wall surface 31. Also, when the position of the air mix door 15 is located at any position other than the maximum cooling position, ions generated by the ion generator 40 can be avoided from disappearing due to collision of part of the warm air, flowing through the heater core 14, with the rear wall surface 31.

Third Embodiment

An interior air-conditioning unit 10 of the present embodiment differs from that of the first embodiment in the mounting position of the ion generator 40, but is the same as that of the first embodiment in other structures.

Figure 6:
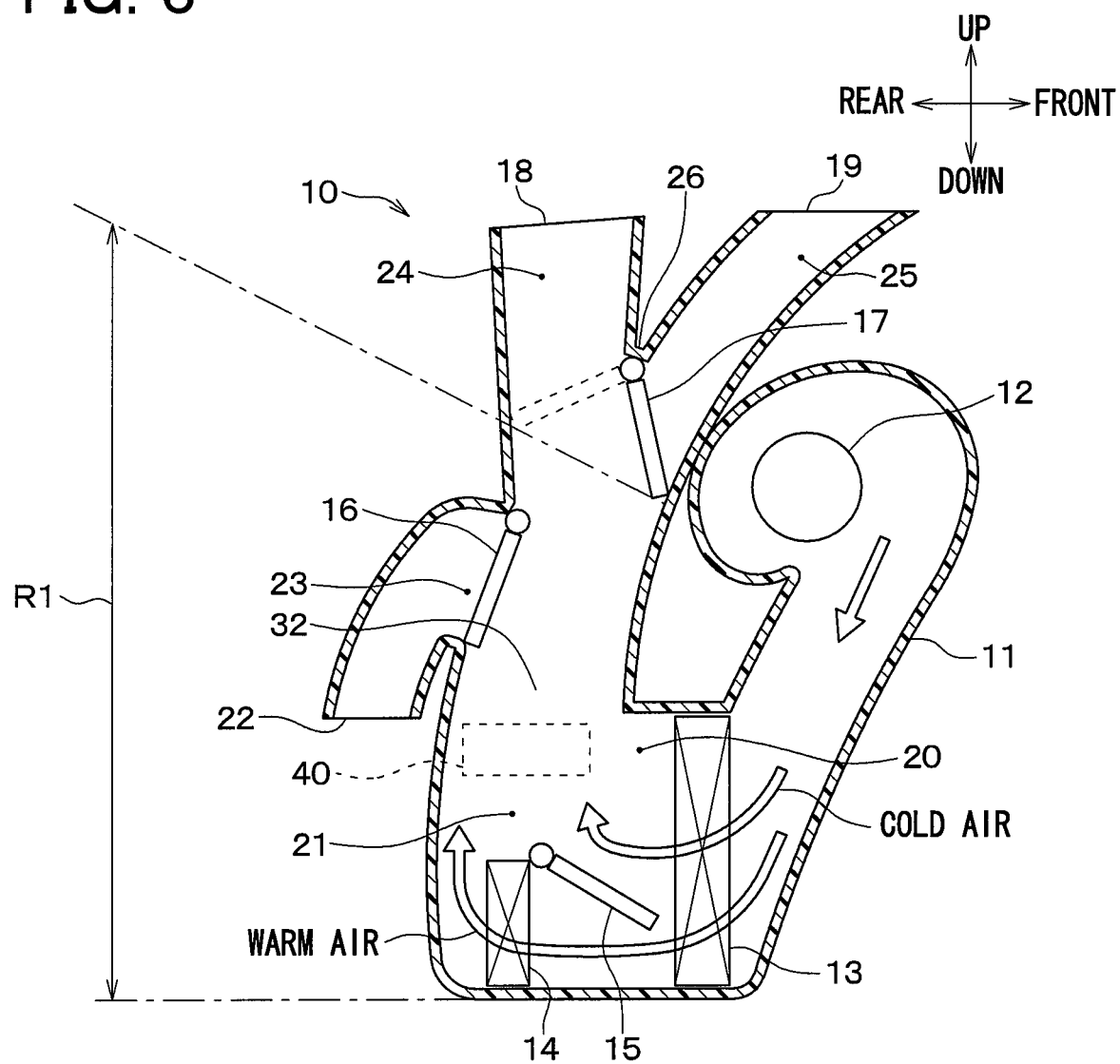
FIG. 6 is a cross-sectional view of an interior air-conditioning unit in a third embodiment.

As shown in FIG. 6, in the interior air-conditioning unit 10 of the present embodiment, the mounting position of the ion generator 40 is at the lateral-side wall surface 32 connected laterally adjacent to the rear wall surface 31. As mentioned in the first embodiment, the flow speed of the airflow having passed through the evaporator 13 and the heater core 14 becomes highest in the vicinity of the rear wall surface 31 and lateral-side wall surfaces 32 and 33. Thus, the present embodiment can also obtain the same effects as the first embodiment.

The mounting position of the ion generator 40 may be any position of the lateral-side wall surface 32 within the range R1 where the air having passed through the evaporator 13 and the heater core 14 flows upward.

Fourth Embodiment

Figure 7:
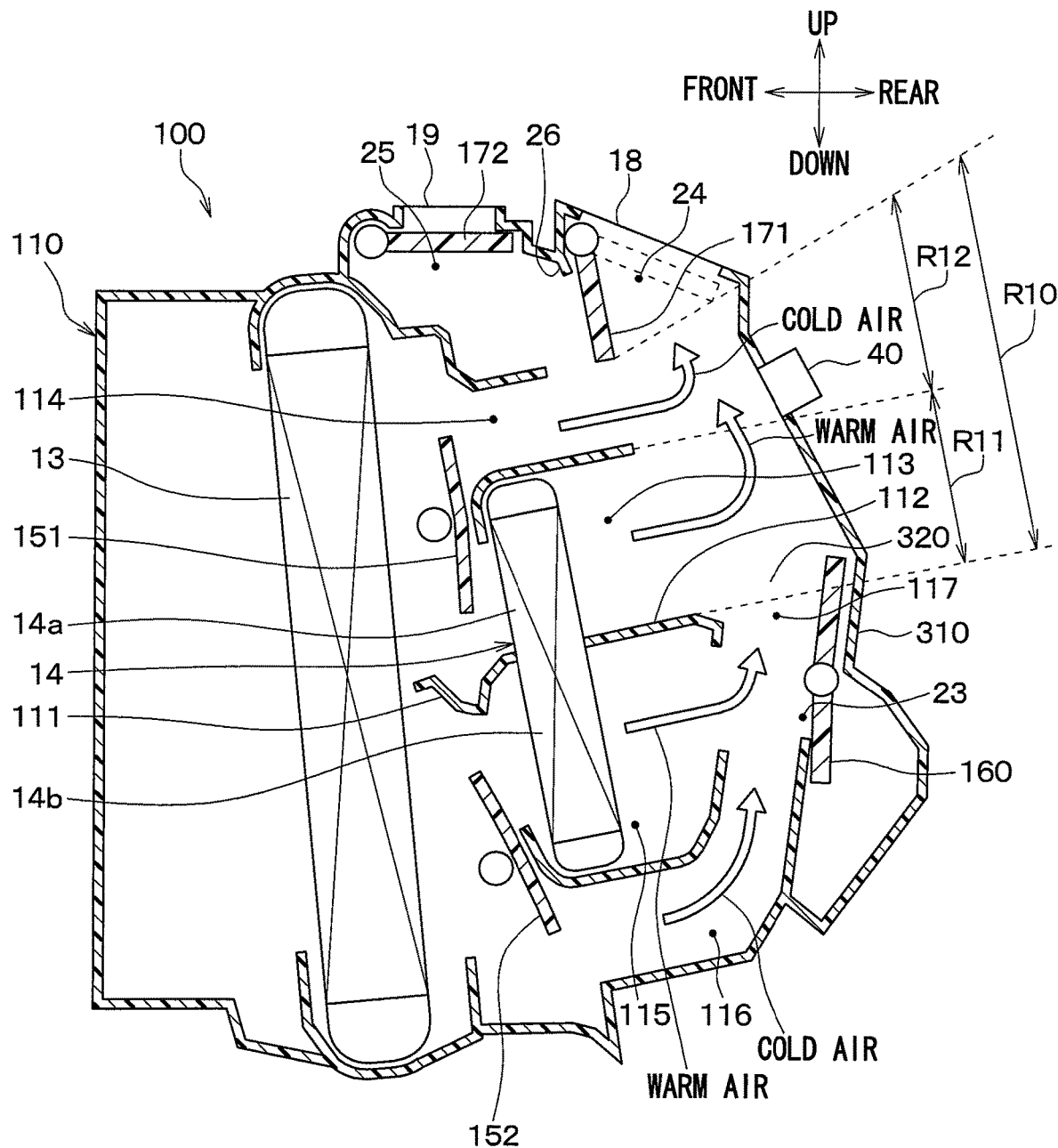
FIG. 7 is a cross-sectional view of an interior air-conditioning unit in a fourth embodiment.

As shown in FIG. 7, in an interior air-conditioning unit 100 of the present embodiment, the airflow having passed through the evaporator 13 is divided into upper and lower two-layer flows.

The air-conditioning unit 100 includes the evaporator 13 and the heater core 14 which are disposed in an air-conditioning case 110. Although not shown, the fan is disposed while being offset in the right-left direction of the vehicle with respect to the evaporator 13 and the heater core 14. The evaporator 13 and the heater core 14 are disposed on the lower side of the face opening 18 and the defroster opening 19 formed at the upper part of the air-conditioning case 110. The evaporator 13 and the heater core 14 are disposed to allow the air to pass therethrough in the lateral direction from the front side to the rear side. The heater core 14 is disposed on the vehicle rear side with respect to the evaporator 13.

Within the air-conditioning case 110, partition walls 111 and 112 are formed to divide the airflow having passed through the evaporator 13 into upper and lower two-layer flows.

An upper-side warm-air flow passage 113 and an upper-side cold-air flow passage 114 are formed as the upper-side flow passage on the upper side of the partition walls 111 and 112. The upper-side warm-air flow passage 113 causes the warm air having passed through an upper-side part 14a of the heater core 14 to flow therethrough. The upper-side cold-air flow passage 114 causes the cold air having passed through the evaporator 13 to flow while bypassing the heater core 14. The upper-side cold-air flow passage 114 is formed on the upper side of the heater core 14. A lower-side warm-air flow passage 115 and a lower-side cold-air flow passage 116 are formed as the lower-side flow passage on the lower side of the partition walls 111 and 112. The lower-side warm-air flow passage 115 causes the warm air having passed through a lower-side part 14b of the heater core 14 to flow therethrough. The lower-side cold-air flow passage 116 causes the cold air having passed through the evaporator 13 to flow while bypassing the heater core 14.

The lower-side cold-air flow passage 116 is formed on the lower side of the heater core 14.

First and second air mix doors 151 and 152 are disposed on the upper side of the heater core 14 inside the air-conditioning case 110. The first air mix door 151 adjusts the ratio of air volume of the warm air flowing through the upper-side warm-air flow passage 113 to the cold air flowing through the upper-side cold-air flow passage 114. The second air mix door 152 adjusts the ratio of air volume of the warm air flowing through the lower-side warm-air flow passage 115 to the cold air flowing through the lower-side cold-air flow passage 116.

Also in the present embodiment, the air-conditioning case 110 has a rear wall surface 310 positioned on the rear side, and lateral-side wall surfaces positioned on both sides in the right-left direction, as wall surfaces configuring a downstream side flow passage on the downstream side of the airflow with respect to the evaporator 13 and the heater core 14. FIG. 7 illustrates a lateral-side wall surface 320 positioned as one side (i.e., right sight) of the lateral-side wall surfaces positioned on both sides in the right-left direction. The rear wall surface 310 extends along the up-down direction and the right-left direction. The lateral-side wall surface 320 extends along the up-down direction and the front-rear direction. The rear wall surface 310 and the lateral-side wall surface 320 extend from the bottom part to the upper part of the air-conditioning case 110.

The partition wall 112 is provided with an upper-lower communication port 117 that communicates the upper flow passage with the lower flow passage. A part of the rear wall surface 310 on the lower side with respect to the partition wall 112 is provided with a foot communication port 23 that communicates with the foot opening. A foot door 160 is disposed between the upper-lower communication port 117 and the foot communication port 23 inside the air-conditioning case 110. The foot door 160 selectively opens and closes the upper-lower communication port 117 and the foot communication port 23.

The face flow passage 24 directed toward the face opening 18 and the defroster flow passage 25 directed toward the defroster opening 19 are formed on the upper side of the inside of the air-conditioning case 110. In other words, the air-conditioning case 110 includes the partition 26 that separates the face flow passage 24 and the defroster flow passage 25. A face door 171 is disposed in the face flow passage 24 so as to open and close the face opening 18. A defroster door 172 is disposed in the defroster flow passage 25 so as to open and close the defroster opening 19. The face door 171 and the defroster door 172 configure doors that switch between opening and closing of the face opening 18 and the defroster opening 19, respectively.

As shown in FIG. 7, in the face mode, the defroster opening 19 is closed, the face opening 18 is open, and the foot communication port 23 is closed. Thus, the cold air in the upper-side cold-air flow passage 114, the warm air in the upper-side warm-air flow passage 113, the cold air in the lower-side cold-air flow passage 116, t and the warm air in the lower-side warm-air flow passage 115 flow toward the face opening 18. At this time, in the upper-side flow passage, the warm air flowing through the upper-side warm-air flow passage 113 from the front side to the rear side and the cold air flowing through the upper-side cold-air flow passage 114 from the front side to the rear side collide with the rear wall surface 310 and change their directions upward. The same goes for the defroster mode. Therefore, also in the present embodiment, the rear wall surface 310 configures a collision-side wall surface with which the airflow having passed through the heat exchanger collides to be directed upward.

In the interior air-conditioning unit 100 of the present embodiment, the ion generator 40 is mounted on the rear wall surface 310. The ion generator 40 adds ions to the air flowing through the upper-side flow passage. Thus, a mounting position of the ion generator 40 is located on the upper side with respect to the partition wall 112 and within a range R10 on the upstream side of the airflow with respect to the partition 26 and the face door 171. More specifically, the mounting position of the ion generator 40 is located at the rear wall surface 310 within a range R12 on the downstream side of the airflow directed toward the face opening 18 with respect to a range R11 in the rear wall surface 310 that faces the upper-side part 14a of the heater core 14 via a space in the airflow direction inside the heater core 14.

In the present embodiment, the ion generator 40 is mounted to the rear wall surface 310. Thus, the present embodiment can also exhibit the same effects as the first embodiment.

The mounting position of the ion generator 40 may be any position of the rear wall surface 310 within the range R10 mentioned above. The mounting position of the ion generator 40 is preferably located within the range R12 on the downstream side of the airflow with respect to the range R11 of the rear wall surface 310 that faces the upper-side part 14a of the heater core 14 via the space. The range R11 of the rear wall surface 310 that faces the upper-side part 14a of the heater core 14 via the space is a range with which part of the warm air having passed through the heater core 14 collides. For this reason, the mounting position of the ion generator 40 is positioned within the range R12, thereby preventing ions generated by the ion generator 40 from colliding with the rear wall surface 310 and disappearing there.

Figure 8:
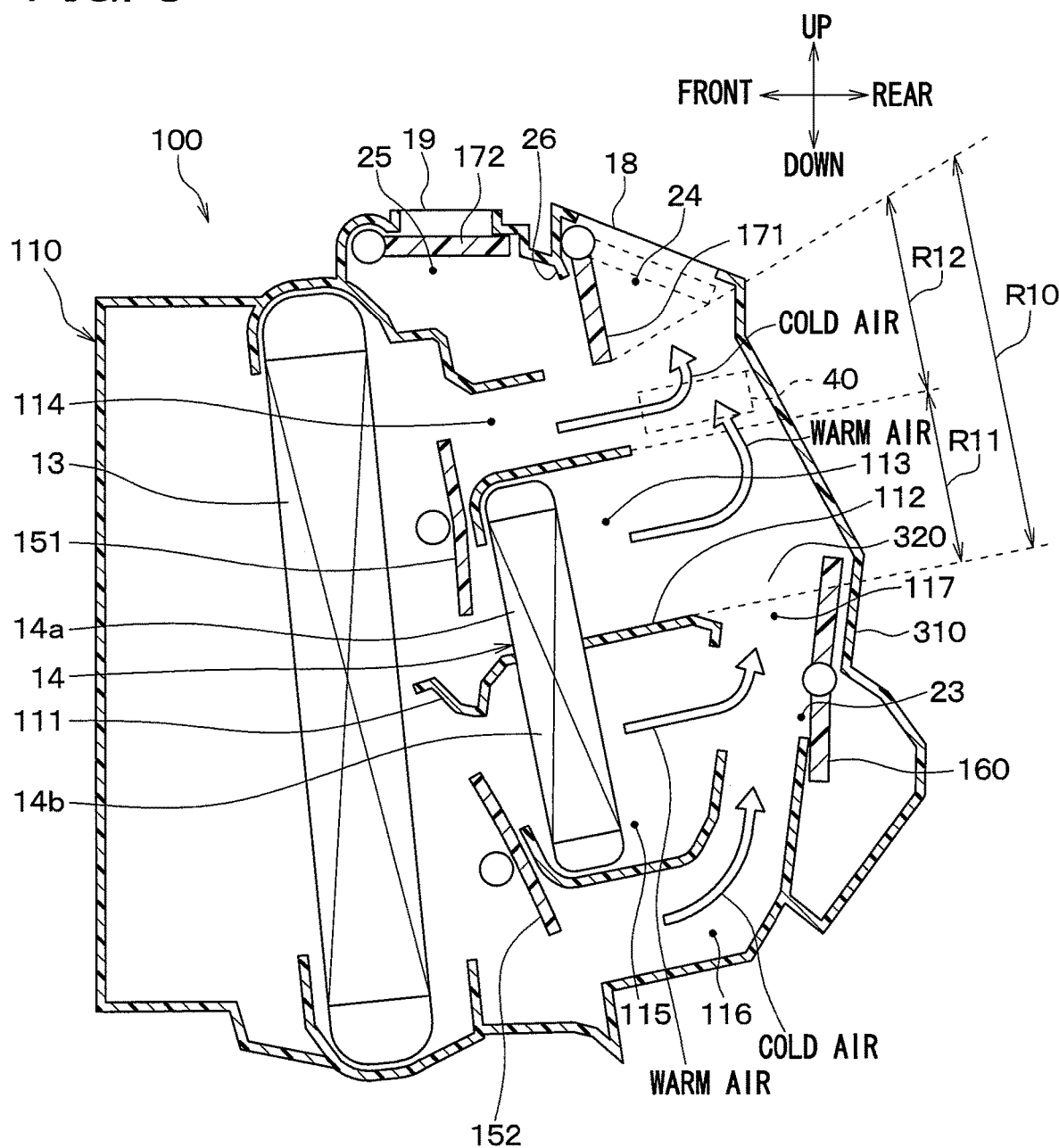
FIG. 8 is a cross-sectional view of an interior air-conditioning unit in a fifth embodiment.

As shown in FIG. 8, the mounting position of the ion generator 40 may be at the lateral-side wall surface 320 laterally adjacent to the rear wall surface 310. As described in the first embodiment, the flow speed of the airflow having passed through the evaporator 13 and the heater core 14 becomes highest in the vicinity of the rear wall surface 310 and lateral-side wall surfaces 320.

In the interior air-conditioning unit 100 of the present embodiment, each of the face door 171 and the defroster door 172 is configured of a plate door, but may be configured of a rotary door.

Fifth Embodiment

Figure 9:
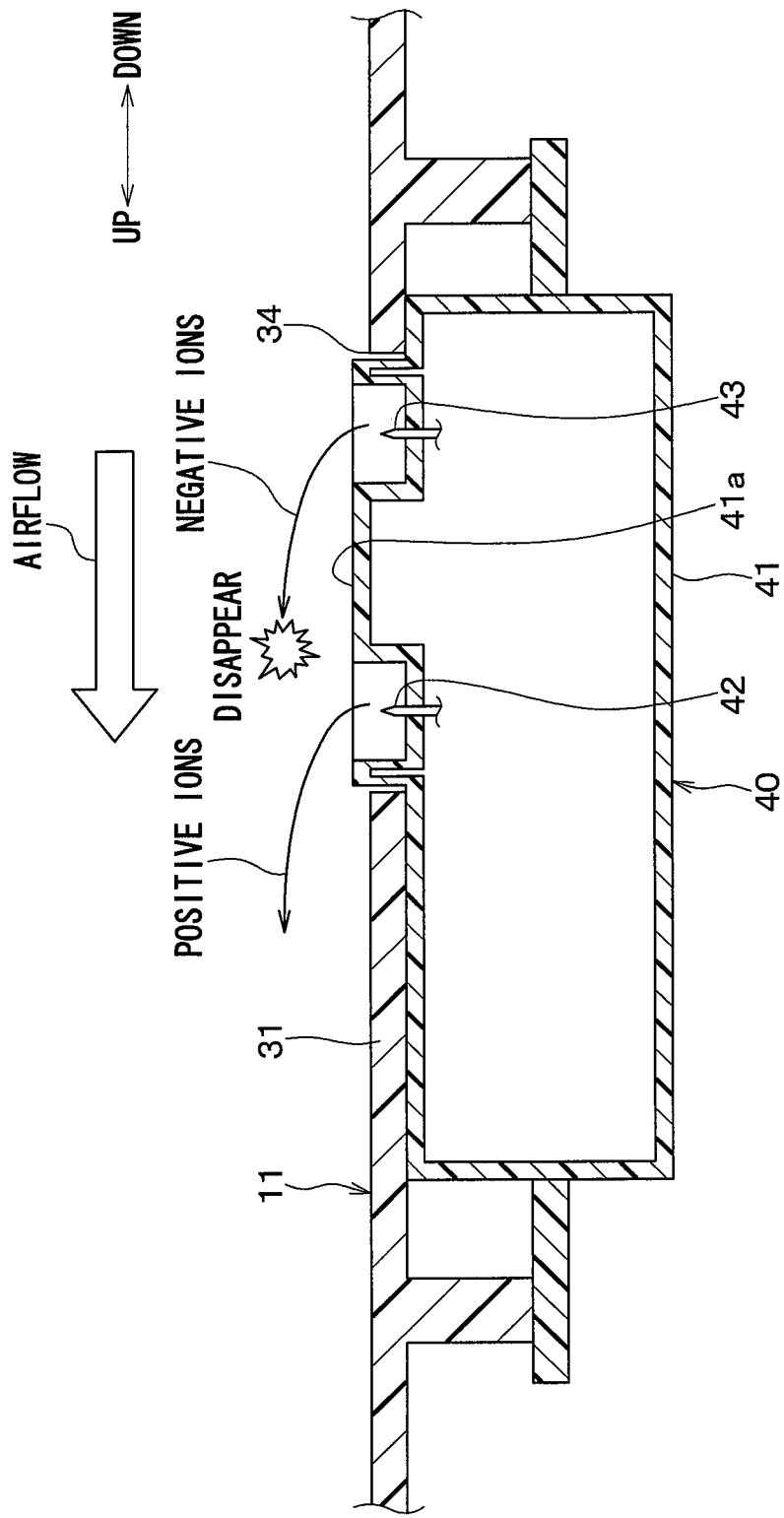
FIG. 9 is a cross-sectional view of an ion generator and its surroundings in a sixth embodiment.

As shown in FIG. 9, in a present embodiment, the arrangement of the anode 42 and the cathode 43 in the ion generator 40 is changed with respect to the interior air-conditioning unit 10 in the first embodiment. The interior air-conditioning unit 10 of the present embodiment is the same as that of the first embodiment in other structures.

In the present embodiment, the cathode 43 is disposed on the upstream side of the airflow (specifically, main flow) toward the face opening 18 and the defroster opening 19 with respect to the anode 42. More specifically, the direction of the airflow in a region where the ion generator 40 is mounted is one oriented from the lower side to the upper side. Thus, the cathode 43 is disposed on the lower side of the anode 42.

The ion generator 40 has properties in which an amount of negative ions generated in the cathode 43 is larger than an amount of positive ions generated in the anode 42. The ion generator 40 in the present embodiment exhibits the sterilization effect of decomposing and removing mold fungi and viruses floating within a vehicle interior space in the air by using both the positive ions and negative ions.

Unlike the present embodiment, in a case where the anode 42 is disposed on the upstream side with respect to the cathode 43, some of positive ions generated in the anode 42 flow to the cathode 43 to be cancelled out by the cathode 43. In this case, the positive ions, the generated amount of which is originally smaller than that of the negative ions, are allowed to disappear, thus causing a large difference between the amounts of positive ions and negative ions. Thus, the sterilization effect obtained by both the positive ions and the negative ions is reduced.

In contrast, in the present embodiment, some of the negative ions generated in the cathode 43 are cancelled out by the anode 42 to disappear, while the positive ions generated by the anode 42 never disappear due to the cathode 43. The generated amount of negative ions is originally larger than the generated amount of positive ions. Thus, even if some of the negative ions disappear, there is no large difference between the amounts of positive ions and negative ions.

Thus, the present embodiment can sufficiently exhibit the sterilization effect by using both the positive ions and the negative ions, compared to a case where the anode 42 is disposed on the upstream side with respect to the cathode 43.

Other Embodiments

The present disclosure is not limited to the above-mentioned embodiments, and various modifications and changes can be appropriately made within the scope of claims as follows.

(1) In each of the above-mentioned embodiments, the mounting position of the ion generator 40 is the position of the part of the rear wall surface 31 on the upstream side of the airflow with respect to the movable regions of the partition 26 and the face/defroster switching door 17, but is not limited thereto. The mounting position of the ion generator 40 may be a position of the part of the rear wall surface 31 on the downstream side of the airflow with respect to the movable regions of the face/defroster switching door 17.

(2) In each of the above-mentioned embodiments, the rear wall surfaces 31 and 310 configure collision-side wall surfaces with which the airflow having passed through the heat exchanger collides to be directed upward. However, other wall surfaces may serve as the collision-side wall surface. For example, when the front-rear direction is changed to the right-left direction in a vehicle mounted state of the interior air-conditioning unit 10 of the first embodiment, the rear wall surface 31 shown in FIG. 1 becomes a right-side wall surface, and the right-side wall surface becomes the collision-side wall surface. The collision-side wall surface is a wall surface positioned on the opposite side to the evaporator via the heater core. In other words, the collision-side wall surface is a wall surface facing respective air outlet portions of the heater core and the evaporator.

(3) The above-mentioned respective embodiments are not irrelevant to each other, and any appropriate combination between them can be implemented except when the combination seems obviously impossible. It is obvious that in the above-mentioned respective embodiments, the elements configuring the embodiments are not necessarily essential particularly unless otherwise specified to be essential, except when clearly considered to be essential in principle, and the like.

SUMMARY

According to a first aspect of a part or all of the above-mentioned respective embodiments, the air conditioner for a vehicle includes the air-conditioning case, the heat exchanger, and the ion generator. The air-conditioning case has the outlet opening at its upper part. The heat exchanger is disposed on the lower side of the outlet opening in the air-conditioning case. The ion generator is mounted on the air-conditioning case such that the electrodes are exposed in air flowing through the air flow passage. The air-conditioning case includes the collision-side wall surface with which the airflow having passed through the heat exchanger collides to be directed upward and the lateral-side wall surfaces connected laterally adjacent to the collision-side wall surface. The ion generator is disposed at the predetermined position of the collision-side wall surface or the lateral-side wall surface.

A second aspect is as follows. The outlet openings include the face opening that communicates with the face air outlet provided in the vehicle interior and the defroster opening that communicates with the defroster air outlet provided in the vehicle interior. The vehicle air conditioner further includes the door disposed in the air-conditioning case and configured to switch between opening and closing of each of the face opening and the defroster opening. The air-conditioning case has the partition that separates the flow passage for guiding the air toward the face opening and the flow passage for guiding the air toward the defroster opening. The predetermined position is a position on the upstream side of the airflow with respect to the partition and the door.

Thus, in a mode of blowing air from at least one of the face opening and the defroster opening while reducing the number of ion generators mounted on the air-conditioning case, air with ions can be blown towards the face of an occupant.

According to a third aspect, the predetermined position is a position on the downstream side of the airflow with respect to the range of the collision-side wall surface that faces the heating heat exchanger via a space. Thus, the ions generated by the ion generator can be prevented from disappearing due to the collision of the airflow having passed through the heating heat exchanger with the collision-side wall surface.

According to a fourth aspect, the predetermined position is a position on the upper side with respect to the heating heat exchanger. This predetermined position can provide the same effects as in the third aspect.

According to a fifth aspect, the ion generator includes one anode and one cathode as the electrodes, and the anode and the cathode are arranged in a direction that intersects the direction of the airflow toward the outlet opening.

Thus, the positive ions formed by the anode can be avoided from flowing to the cathode and disappearing at the cathode. Likewise, the negative ions formed by the cathode can be avoided from flowing to the anode and disappearing at the anode. Thus, a large amount of ions can be discharged from each of the anode and the cathode.

According to a sixth aspect, the ion generator has one anode and one cathode as electrodes and has properties in which an amount of negative ions generated in the cathode is larger than an amount of positive ions generated in the anode. The cathode is disposed on the upstream side of the airflow with respect to the anode.

Conversely, in a case where the anode is disposed on the upstream side of the airflow with respect to the cathode, some of positive ions generated in the anode flow to the cathode to be cancelled out by the cathode. In this case, the positive ions, the generated amount of which is originally smaller than that of the negative ions, are allowed to disappear, thus causing a large difference between the amounts of positive ions and negative ions. Thus, the effect obtained by both the positive ions and the negative ions is reduced.

In contrast, according to a sixth aspect, some of the negative ions generated in the cathode are cancelled out by the anode to disappear, but there is no large difference between the amounts of positive ions and negative ions, even when some of the negative ions disappear. Thus, the effect obtained by both the positive ions and the negative ions can be sufficiently exhibited, compared to the case where the anode is disposed on the upstream side of the airflow with respect to the cathode.

What is claimed is:

1. An air conditioner for a vehicle, for blowing air with ions into a vehicle interior, the air conditioner comprising:
   an air-conditioning case that defines therein an air flow passage through which air toward the vehicle interior flows, and has an outlet opening at an upper part of the air-conditioning case and through which the air toward the vehicle interior passes;
   a heat exchanger disposed at a lower side of the outlet opening in the air-conditioning case, the heat exchanger being configured to exchange heat between air toward the vehicle interior and a heat-exchange medium; and
   an ion generator that includes electrodes configured to generate ions, the ion generator being mounted on the air-conditioning case such that the electrodes are exposed in the air flowing through the air flow passage, wherein
   the air-conditioning case has a collision-side wall surface with which an airflow having passed through the heat exchanger collides to be directed upward, and a lateral-side wall surface connected to and laterally adjacent to the collision-side wall surface,
   the ion generator is disposed at a predetermined position of the collision-side wall surface or the lateral-side wall surface,
   the ion generator includes one anode and one cathode as electrodes and has properties in which an amount of negative ions generated in the cathode is larger than an amount of positive ions generated in the anode, and
   the cathode is disposed on an upstream side of the airflow toward the outlet opening with respect to the anode.

2. The air conditioner for a vehicle according to claim 1, wherein
   the outlet opening includes a face opening that communicates with a face air outlet provided in the vehicle interior and a defroster opening that communicates with a defroster air outlet provided in the vehicle interior, the air conditioner further comprising:
   a door disposed inside the air-conditioning case, the door being configured to switch between opening and closing of each of the face opening and the defroster opening, wherein
   the air-conditioning case includes a partition that separates a flow passage that guides air toward the face opening and a flow passage that guides air toward the defroster opening, and
   the predetermined position is a position located on an upstream side of the airflow with respect to the partition and the door.

3. The air conditioner for a vehicle according to claim 1, wherein
   the heat exchanger includes a cooling heat exchanger that cools the air and a heating heat exchanger that heats the air having passed through the cooling heat exchanger,
   the air-conditioning case includes a cold-air flow passage formed at an upper side of the heating heat exchanger and through which the air having passed through the cooling heat exchanger flows while bypassing the heating heat exchanger, and
   the predetermined position is a position located on an upper side with respect to the heating heat exchanger.

4. The air conditioner for a vehicle according to claim 1, wherein
   the anode and the cathode are arranged side by side in a direction that intersects a direction of the airflow toward the outlet opening.

5. An air conditioner for a vehicle, for blowing air with ions into a vehicle interior, the air conditioner comprising:
   an air-conditioning case that defines therein an air flow passage through which air toward the vehicle interior flows, and has an outlet opening at an upper part of the air-conditioning case and through which the air toward the vehicle interior passes;
   a heat exchanger disposed at a lower side of the outlet opening in the air-conditioning case, the heat exchanger being configured to exchange heat between air toward the vehicle interior and a heat-exchange medium; and
   an ion generator that includes electrodes configured to generate ions, the ion generator being mounted on the air-conditioning case such that the electrodes are exposed in the air flowing through the air flow passage, wherein
   the air-conditioning case has a collision-side wall surface with which an airflow having passed through the heat exchanger collides to be directed upward, and a lateral-side wall surface connected to and laterally adjacent to the collision-side wall surface,
   the heat exchanger includes a cooling heat exchanger that cools the air and a heating heat exchanger that heats the air having passed through the cooling heat exchanger,
   the air-conditioning case includes a cold-air flow passage formed on an upper side of the heating heat exchanger and through which the air having passed through the cooling heat exchanger flows while bypassing the heating heat exchanger,
   wherein a portion of the collision-side wall surface and a portion of the lateral-side wall surface facing a core surface of the heating heat exchanger form a space, and the ion generator is disposed at a predetermined position on the collision-side wall surface or the lateral-side wall surface, on a downstream side of the space.

6. The air conditioner for a vehicle according to claim 3, wherein
   the outlet opening includes a face opening that communicates with a face air outlet provided in the vehicle interior and a defroster opening that communicates with a defroster air outlet provided in the vehicle interior, the air conditioner further comprising:
   a door disposed inside the air-conditioning case, the door being configured to switch between opening and closing of each of the face opening and the defroster opening, wherein
   the air-conditioning case includes a partition that separates a flow passage that guides air toward the face opening and a flow passage that guides air toward the defroster opening, and the predetermined position is a position located on an upstream side of the airflow with respect to the partition and the door.

7. The air conditioner for a vehicle according to claim 3, wherein
the predetermined position is a position located on an upper side with respect to the heating heat exchanger.

8. The air conditioner for a vehicle according to claim 3, wherein
the ion generator includes one anode and one cathode as electrodes, and
the anode and the cathode are arranged side by side in a direction that intersects a direction of the airflow toward the outlet opening.

* * * * *